(12) United States Patent
Van Lieshout et al.

(10) Patent No.: US 10,690,663 B2
(45) Date of Patent: Jun. 23, 2020

(54) MANUFACTURING OF A BIOSENSOR CARTRIDGE

(71) Applicant: KONINKLIJKE PHILIPS N.V., Eindhoven (NL)

(72) Inventors: Ron Martinus Laurentius Van Lieshout, Geldrop (NL); Emiel Peeters, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 129 days.

(21) Appl. No.: 15/560,301

(22) PCT Filed: Mar. 25, 2016

(86) PCT No.: PCT/EP2016/056733
§ 371 (c)(1),
(2) Date: Sep. 21, 2017

(87) PCT Pub. No.: WO2016/151143
PCT Pub. Date: Sep. 29, 2016

(65) Prior Publication Data
US 2018/0067110 A1 Mar. 8, 2018

(30) Foreign Application Priority Data
Mar. 26, 2015 (EP) ..................... 15160948

(51) Int. Cl.
*G01N 33/553* (2006.01)
*G01N 33/543* (2006.01)
*G01N 33/53* (2006.01)

(52) U.S. Cl.
CPC ... *G01N 33/54326* (2013.01); *G01N 33/5306* (2013.01); *G01N 33/5434* (2013.01); *G01N 33/54366* (2013.01)

(58) Field of Classification Search
None
See application file for complete search history.

(56) References Cited

U.S. PATENT DOCUMENTS 7,993,525 B2 * 8/2011 Su ................ G01N 1/4044
210/695
8,945,946 B2 2/2015 Ikeda
(Continued)

FOREIGN PATENT DOCUMENTS

WO 2006079998 A2 8/2006
WO 2006134546 A2 12/2006
(Continued)

OTHER PUBLICATIONS

Bruls et al "Rapid Integrated Biosensor for Multiplexed Immunoassays based on Actuated Magnetic Nanoparticles" Lab on a Chip, vol. 9, No. 24, Jan. 1, 2009, pp. 3504-3510.
(Continued)

*Primary Examiner* — Christopher L Chin

(57) ABSTRACT

The invention relates to a processing device (110) and a method for manufacturing such a device. In a preferred embodiment, a mixture of magnetic particles (MP), a matrix material, and a volatile carrier is deposited onto binding sites (112) of a reaction surface (113). The deposited mixture is then dried while the magnetic particles (MP) are pulled away from the reaction surface (113) by a magnetic field (B). Thus unspecific binding of magnetic particles to the binding sites can be prevented.

10 Claims, 3 Drawing Sheets

(56) References Cited

U.S. PATENT DOCUMENTS

| | | | |
|---|---|---|---|
| 9,488,647 B2 | 11/2016 | Van Zon et al. | |
| 9,841,419 B2 | 12/2017 | Kelly et al. | |
| 9,964,539 B2 | 5/2018 | Hamasaki et al. | |
| 2004/0126797 A1 | 7/2004 | Hsu et al. | |
| 2009/0263834 A1 | 10/2009 | Sista | |
| 2010/0289483 A1* | 11/2010 | Immink | G01R 33/1269 324/204 |
| 2011/0306070 A1 | 12/2011 | Campbell | |
| 2013/0146461 A1 | 6/2013 | Pamula | |

FOREIGN PATENT DOCUMENTS

| | | |
|---|---|---|
| WO | 2008115723 A1 | 9/2008 |
| WO | 2009024922 A2 | 2/2009 |
| WO | 2009125339 A2 | 10/2009 |
| WO | 2010086772 A1 | 8/2010 |
| WO | 2011036634 A1 | 3/2011 |
| WO | 2014037880 A1 | 3/2014 |

OTHER PUBLICATIONS

Ariel Hecht Label-Acquired Magnetorotation (LAM), 2013.
Gao, Yang et al "Disaggregation of Microparticle Clusters by Induced Magnetic Dipole-Dipole Repulsion near a Surface", Lab on a Chip, Vol. 13, 2013, pp. 1394-1401.

\* cited by examiner

MANUFACTURING OF A BIOSENSOR CARTRIDGE

CROSS-REFERENCE TO PRIOR APPLICATIONS

This application is the U.S. National Phase application under 35 U.S.C. § 371 of International Application No. PCT/EP2016/056733, filed on Mar. 25, 2016, which claims the benefit of European Patent Application No. 15160948.4, filed on Mar. 26, 2015. These applications are hereby incorporated by reference herein.

FIELD OF THE INVENTION

The invention relates to a processing device comprising magnetic particles, particularly to a biosensor cartridge. Moreover, it relates to a method for manufacturing such a device.

BACKGROUND OF THE INVENTION

The WO 2006/134546 A2, WO2006/079998 and Bruls et al. ("Rapid integrated biosensor for multiplexed immunoassays based on actuated magnetic nanoparticles", Lab Chip, 2009, 9, 3504-3510—Oct. 13, 2009) disclose magnetic biosensors with a sensing surface that is coated with binding sites which can specifically bind to target components either carried by magnetic beads or labeled by magnetic beads. Documents further disclose various procedures to dynamically distinguish between magnetic beads which are specifically or un-specifically bound to the binding sites, respectively.

SUMMARY OF THE INVENTION

It would be advantageous to provide means that allow for a detection of analyte of interest with higher accuracy.

This object is addressed by a method according to claim 1 and a processing device according to claim 7. Preferred embodiments are disclosed in the dependent claims.

According to a first aspect, the invention relates to a method for manufacturing a processing device that comprises magnetic particles. The method comprises the following steps:

a) Depositing a quantity of a liquid mixture comprising magnetic particles, a first material, and a second material onto a surface ("deposition surface") of the processing device. The first material will in the following be called "matrix material" because it serves as a kind of matrix after accomplishment of the device, and the second material will be called "volatile carrier" because it mainly serves as a carrier for the magnetic particles and the matrix material that later on evaporates.

"Matrix material" may be for example a sugar compound (e.g. sucrose, trehalose, dextrans, sorbitol, etc. and combination thereof), or an amorphous vitrified material in a broader sense with a glass transition temperature above room temperature, or a polymer As it is known in the literature, a "volatile material" is more volatile than water. For example, an organic solvent can be used if the matrix material is a polymer.

Therefore, after the volatile material has been removed, a "glassy substrate" (matrix) typically remains.

The "deposition surface" may be made of any type of material, for instance COP ("cyclo-olefin copolymer"), polystyrene, PMMA, glass, cellulose.

b) Pulling the aforementioned magnetic particles of the mixture to a desired location within the mixture.

c) Drying the mixture by removing the volatile carrier.

The steps of the method may be executed in the listed or any other appropriate order. In particular, the pulling step b) may (at least temporarily) be executed in parallel to the depositing step a), in parallel to the drying step c), or in parallel to both the depositing step a) and the drying step c). Most preferably, it is executed in parallel to the drying step c).

The processing device may in general serve any purpose, particularly the processing of a sample or substance using the magnetic particles comprised by the device. A typical example of such a processing is the detection of target molecules in a biological sample with the help of magnetic particles that specifically bind to said molecules.

The term "magnetic particles" shall comprise both permanently magnetic particles as well as magnetizable particles, for example superparamagnetic beads. The size of the magnetic particles typically ranges between 3 nm and 50 µm, in particular between 100 nm to 2 µm, or in particular around 500 nm. Moreover, the magnetic particles may comprise binding molecules for target components one is actually interested in.

The term "drying" shall imply that, after removal of the volatile carrier, the initially liquid mixture solidifies, leaving behind matrix material and magnetic particles. In a typical application, the mixture comprises magnetic particles and other components which after evaporation of the volatile carrier (e.g. water) create a matrix which fixates the magnetic particles and keeps the biological components stable.

The pulling of the magnetic particles to a desired location within the mixture may be done by an appropriate magnetic field, which usually requires that said magnetic field has a non-zero gradient at the location of the magnetic particles. Additionally or alternatively, the pulling may be achieved by the effect of gravity and/or by inertial or centrifugal forces. In this case matrix material and magnetic particles are separated from each other according to their density, with the material of higher density taking a position below the material of lower density with respect to the direction of the effective force. In the typical case that the magnetic particles have a higher density than the matrix material, drying may for example be done in an upside down arrangement of (from top to bottom with respect to gravity) the deposition surface, the matrix material, and the magnetic beads.

The magnetic particles may be pulled to any location within the mixture that is desired due to given design or processing criteria. In particular, the magnetic particles of the mixture may be pulled away from the deposition surface. This yields a processing device comprising magnetic particles which do not immediately contact the deposition surface because the magnetic particles are pulled away from it, e.g. by a magnetic field, wherein this configuration is fixed or "frozen" during the drying step. It turns out that preventing a contact of the magnetic particles to the deposition surface has several advantages, which will be discussed in more detail below with respect to particular embodiments of the invention. In other words, the term "Away" means that the magnetic particles are sufficiently far from the surface for not having specific and non-specific binding (or interaction) with it (chemically and/or physically). It is in particular preferable that the beads do not touch the surface during the process.

According to a preferred embodiment of the method, the magnetic field that may be generated during the pulling step b) has a non-zero gradient that is substantially perpendicular to the deposition surface. The magnetic particles will then tend to form chains that extend substantially parallel to the deposition surface.

In general, the deposition surface may be any kind of surface of a solid body that is suited for the intended application of the processing device, for example a surface on a cover (or laminate) of a cartridge. In a preferred embodiment, the surface onto which the mixture is deposited may be a surface called "reaction surface" because physical and/or chemical reactions take place at it during usage of the processing device. Moreover, said reaction surface may at least locally be coated with binding sites that can specifically bind target substances. The reaction surface may for instance comprise one or more spots coated with such binding sites. The binding sites may particularly be molecules that can specifically bind to target components in a sample, for example antibodies that bind to associated antigens.

There are several possibilities how the aforementioned binding sites can be used in combination with magnetic particles for the detection of a target substance in a sample. In a competition assay, the magnetic particles may for example have surface molecules that compete with the target substance for the binding sites. The higher the concentration of the target substances in a given sample, the less magnetic particles will have a chance to bind to the reaction surface. A quantitative determination of the magnetic particles bound to the reaction surface will hence allow for the determination of the concentration of target substances. Another example is a sandwich assay in which a target substance is needed to link a binding site to a magnetic particle.

In another embodiment of the invention, the deposition surface is treated, before the depositing step a), with a blocking substance that (preferably reversibly) binds to "binding points". In this context, the term "binding point" is used as a generic expression for any entity on the deposition surface to which components of an assay can permanently or temporarily bind, including (specific and unspecific) binding sites for magnetic beads with or without analyte. The treatment with blocking substance prevents that magnetic particles form undesired (specific or unspecific) bindings to said binding points on the deposition surface while they are still free to move within the liquid mixture that is applied in step a). By reducing the number of such undesired bindings, the level of detection of an assay can be increased due to a reduction of the blank (i.e. assay response when no analyte of interest is available). The blocking substance may at least partially stay on the binding points to prevent (un)specific binding during the execution of the actual assay that shall be performed with a processing device.

The volatile carrier may be any substance suited for the application at hand that is compatible with the matrix material and the magnetic particles. In particular, the volatile carrier may be or comprise an aqueous liquid such as water. The drying step c) can simply comprise the naturally occurring evaporation of water from the mixture, possibly assisted or accelerated by an increase of temperature and/or forced ventilation.

According to a second aspect, the invention relates to a processing device, particularly to a biosensor cartridge, which comprises the following components:

A surface (i.e. a component or body with a surface, said surface in the following being called "deposition surface").

A layer of a matrix material that is disposed on said deposition surface.

Magnetic particles that are disposed in a (proper) sub-region of the matrix material (e.g. in the top part of the matrix layer). The magnetic particles will hence have a non-uniform distribution within the matrix material, having a higher concentration in said sub-region and a lower concentration in the (non-empty) remainder of the matrix material. Preferably, the concentration of magnetic particles outside said sub-region is zero.

The processing device may particularly be manufactured by the method described above. Explanations provided for the method and its variations are therefore analogously valid for the processing device, too, and vice versa. The processing device has the advantage that the non-uniform distribution of magnetic particles can be used to favorably affect the processing steps executed in the device.

According to a preferred embodiment of the processing device of the second aspect or of a processing device manufactured with a method according to the first aspect, the magnetic particles form chains that are oriented substantially parallel to the deposition surface. In the method, this condition shall particularly be fulfilled after completion of the drying step c), but it may be fulfilled during the other steps, too.

In another preferred embodiment, the magnetic particles are disposed a distance away from the deposition surface. Hence matrix material is arranged between the deposition surface and the magnetic particles, which has the advantage to prevent undesired bindings of magnetic particles to the surface. In other words, the term "Away" means that the magnetic particles are sufficiently far from the surface for not interacting with it (chemically and/or physically). In this embodiment, the sub-region comprising the magnetic beads may particularly be a top layer of the matrix material, or any other region not in contact with the surface such that the magnetic particles are not interacting with it.

In another embodiment of the method and/or of the processing device, the matrix material comprises at least one material selected from group consisting of sucrose, salt, buffer components, blocking components and assay reagents.

Additionally or alternatively, the matrix material may optionally be water soluble.

According to another embodiment of the method and/or the processing device(s), the processing device may comprise an optical component that allows for the optical detection of magnetic particles bound to a reaction surface of the device. Said optical component may for example comprise a transparent body on which the reaction surface is formed, wherein said body is appropriately shaped to guide light from a light source to the reaction surface and/or to guide light originating at the reaction surface (e.g. from a reflection) to an (e.g. external) light sensor. In this case the processing device may particularly be designed as a cartridge allowing for an optical detection via Frustrated Total Internal Reflection (FTIR) as it is described in detail for example in the WO 2008/155716 A1 or the WO 2008/115723 A1 (which are incorporated into the present text by reference), or the "double refraction detection" with e.g. a wedge-like optical structure at the binding spot (cf. e.g. WO 2009/125339 A2, which is incorporated into the present text by reference). Other examples comprise the optical detection of single beads (cf. e.g. WO 2011/036634A1, which is incorporated into the present text by reference).

In a further embodiment of the invention, the magnetic particles may be disposed upstream of a target location, wherein the term "upstream" is to be understood with respect to the intended flow of a fluid in the processing device. The "target location" may be any position inside the processing device where the presence of magnetic particles is desired during an assay to be executed with the device. The magnetic particles are preferably disposed at such a location that they will be transported, by a fluid filling the processing device, just to the target location. The target location may for example be a spot of binding sites that can specifically bind target substances of a sample.

BRIEF DESCRIPTION OF THE DRAWINGS

These and other aspects of the invention will be apparent from and elucidated with reference to the embodiments described hereinafter.

In the drawings.

Like reference numbers refer in the Figures to identical or similar components.

DETAILED DESCRIPTION OF EMBODIMENTS

The specific detection of marker molecules in bodily fluids may for example be achieved in biosensor platforms such as the Magnotech® technology or a Single Bead Detection developed by the applicant. An example of a marker molecule is troponin-I (cTnI) for the detection of cardio-vascular disease. The detection technique is based on immuno-assays in combination with the optical detection of "magnetic particles" (e.g. super-paramagnetic nanoparticles or beads) on a "reaction surface" of a cartridge. The mentioned platforms use Total Internal Reflection (TIR) illumination by creating an evanescent optical field near the surface.

In a typical embodiment of the aforementioned technologies, the cartridge may consist of a base-part (consisting of fluidic structure, reaction chambers, reactive spots and optical detection), laminate (for closing the cartridge and placing the magnetic beads in the reaction chamber), and a blood housing (for filtering the cell fraction from the plasma fraction in a blood sample). The magnetic beads are disposed on top of the laminate, which is placed on top of the cartridge in such a way that the beads are inside the reaction chamber. To reduce the cost of the cartridge and to simplify the production process, the beads can alternatively be placed on top of a reactive spot that is present on the base-part in the reaction chamber.

In the WO 2009/024922 A1 (which is incorporated into the present application by reference), a method is described for storing magnetic beads close to a reactive site using a magnetic field to make sure the beads are close to the sensor surface for fast reaction and interaction. In some applications, it is observed however that there is a (typically non-specific) interaction of the magnetic beads with the base-part during the drying process. The non-specifically bound magnetic particles may later reduce the level of detection (LoD) and the dynamic range.

Figure 5:
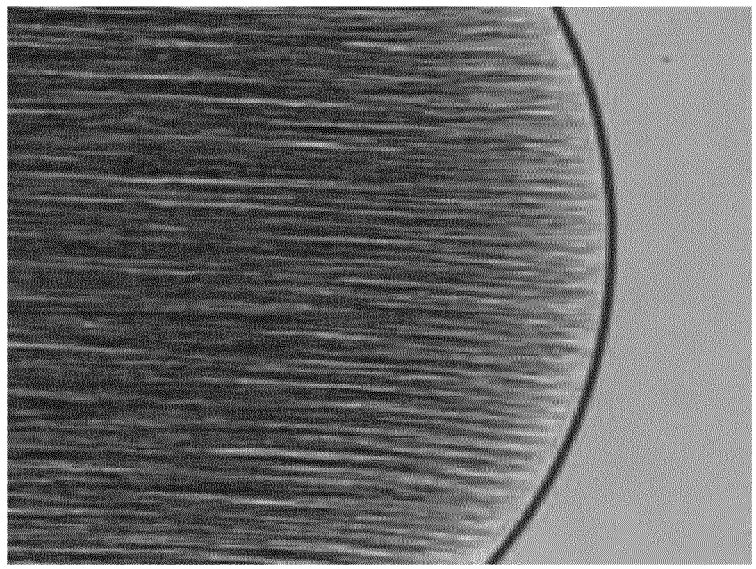
FIG. 5 is a picture taken from a bright field microscope, showing the dried spot with chains of magnetic particles after having used the present invention.
Figure 6:
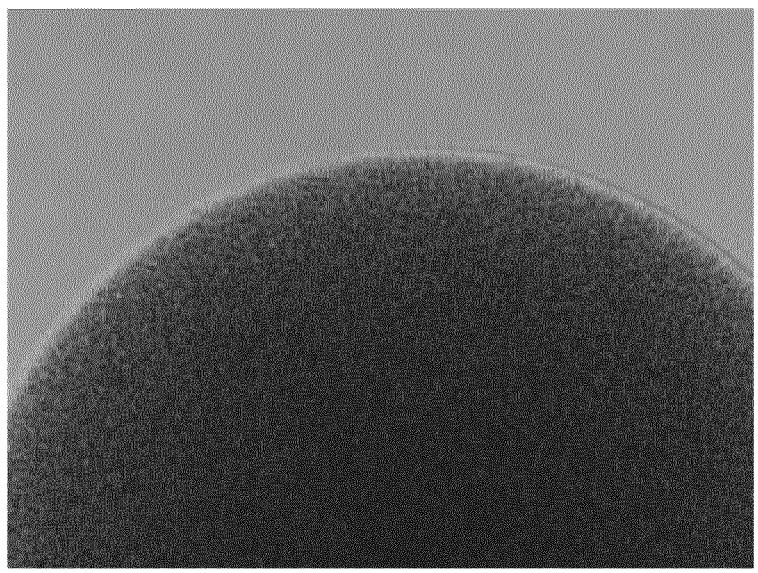
FIG. 6 is a picture taken from a bright field microscope, showing the dried spot without any chain of magnetic particles without having used the present invention.

In order to address the aforementioned issues, an embodiment of the present invention proposes pulling magnetic beads away from the reaction surface, for example by applying a magnetic field on a droplet comprising magnetic beads during drying or by sedimentation (i.e. gravity). This will position the magnetic beads to the top of the droplet preventing interaction with the reaction surface. A glassy state of the dried bead droplet may prevent the magnetic beads from interacting with the reaction surface after the magnetic field has been removed. Moreover, the configuration of the magnet usually creates chains of magnetic beads substantially parallel to the reaction surface which are pulled upward away from the surface (see FIG. 5 in comparison with FIG. 6). Said chains can be detected after drying, e.g. in bright field microscope images, and allow for a distinction of the resulting dried body from a body obtained by ordinary procedures.

Figure 1:
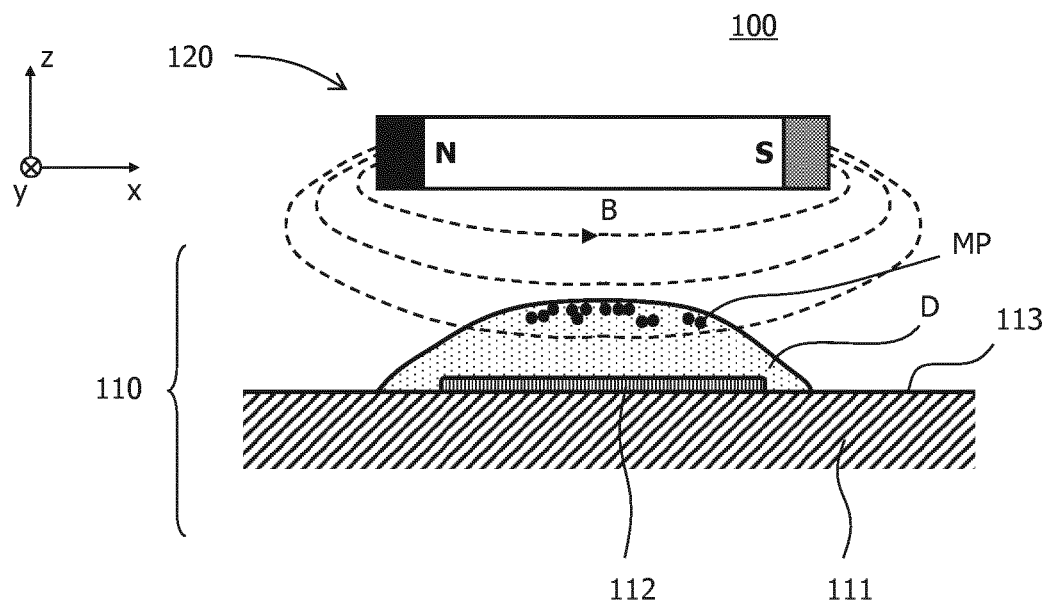
FIG. 1 schematically illustrates the deposition of a droplet comprising magnetic particles on a reaction surface and the pulling of said magnetic particles away from the surface by a magnetic field.

FIG. 1 schematically illustrates a section through the base-part 111 of a cartridge 110 according to an embodiment of the aforementioned concepts. The base-part 111 has a reaction surface 113 that extends in x,y-direction and carries a detection spot with binding sites 112 for target molecules (usually the reaction surface features a plurality of such detection spots with binding sites for the same or for different target molecules). Moreover, a droplet D of a mixture comprising magnetic particles MP, a "matrix material", and a volatile carrier (e.g. water) has been deposited on the binding sites 112.

The Figure further illustrates a magnetic field generator, here a permanent magnet 120, that is arranged (in z-direction) above the droplet D with its axis extending in x-direction parallel to the reaction surface 113. The distance of the magnet 120 from the reaction surface 113 is adjusted such that a magnetic field B is generated within the droplet D that is substantially parallel to the reaction surface and that has a field gradient substantially perpendicular to said surface (i.e. pointing in z-direction). Due to said field gradient, the magnetic particles MP are attracted towards the magnet 120, i.e. pulled away from the reaction surface 113, and collect at the top surface of the droplet D. Thus a contact between the magnetic particles MP and the binding sites 112—and hence an undesired binding of the magnetic particles MP to the binding sites 112—is prevented.

In typical embodiments of a cartridge, the distance between the magnet 120 and the magnetic beads MP is smaller than about 10 mm to properly pull the magnetic beads to one side of the droplet. The distance should however not be too small (e.g. <1 mm) in order to prevent magnetic bead migration outside the droplet.

A magnetic field perpendicular to the reaction surface (i.e. running in z-direction) could also be used. However, the resulting chains of magnetic particles will then usually occupy a larger depth within the droplet perpendicular to the reaction surface (i.e. in z-direction). When applying a magnetic field that is parallel to the reaction surface (as shown in FIG. 1), the magnetic bead chains will occupy a smaller depth, which is preferred in a droplet with limited thickness perpendicular to the reaction surface (the diameter of the droplet D typically ranges between about 50 μm and about 100 μm).

When the configuration of FIG. 1 is maintained for some time, the volatile carrier of the droplet D will eventually evaporate. This process can optionally be supported by a (moderate) increase of temperature of the droplet D and/or a ventilation of dry air along the droplet D.

Optionally, an additional blocking step may be applied to further decrease the chance that a magnetic bead will bind non-specifically to the reaction surface. The blocking step may particularly comprise the addition of an inert protein (e.g BSA, Caseine) which (reversibly) binds to (unspecific) binding points both inside and outside the binding spots. Because the area inside the binding spots may contain proteins (e.g. antibodies as the binding sites 112), this is essentially already blocked.

Figure 2:
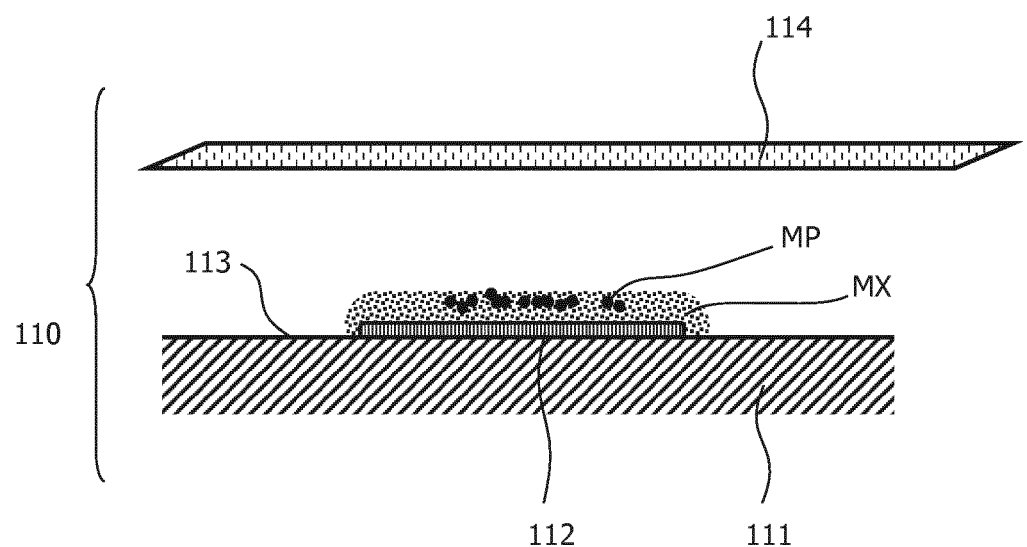
FIG. 2 schematically illustrates a cartridge obtained after completion of the procedure shown in FIG. 1.

FIG. 2 illustrates the situation after a complete removal of the volatile carrier. A solid mass has formed that comprises a body of the matrix material MX immediately above the reaction sites 112 and a layer of magnetic particles MP within a top part of said matrix material. Thus the spatial separation between magnetic particles MP and the binding sites 112 has been permanently fixed. Moreover, the typically glassy body of the matrix material MX prevents degradation of the binding sites (e.g. proteins, antibodies). A laminate or cover 114 is finally attached to the base-part 111 in order to close the reaction chamber(s), channels etc. of the cartridge 110 (these details are not shown in the Figures).

In an alternative embodiment, the laminate or cover 114 is applied onto the base-part 111 before the drying and before or during or after the application of said magnetic field. In that case, the cover 114 may be further arranged to keep or attach the magnetic particles MP onto its surface, optionally through the application of an appropriate magnetic field attracting the magnetic particles MP towards the surface of the cover 114 (and away from the surface of the base-part 111). In this embodiment, the magnetic particles may be applied in the liquid mixture or droplet D on the surface of the cover 114 (instead of on the base-part 111). Thereafter, one may assembly the cover 114 with the base-part 111, apply a magnetic field, during or just after this assembly, to pull the magnetic particles MP of the mixture D to a desired location of the mixture D (e.g. towards the surface of the cover 114), and finally dry. In an alternative, the droplet D can be inserted between the cover 114 and the base-part 111 already assembled one to the other, and the invention is implemented thereafter.

When the cartridge 110 is used, a liquid sample (not shown) will be filled in the reaction chamber, dissolving the magnetic particles MP and the matrix material MX above the binding sites 112. The detection of target components in the sample (or whatever assay is intended) can then proceed.

During usage of the cartridge 110 the problem may arise that if the filling of the cartridge is slow the magnetic beads MP are pulled to the outlet of the reaction chamber, i.e. away from the binding sites 112. Instead of depositing the droplet with the matrix material MX with the magnetic beads MP above the binding sites 112, these components may therefore optionally be disposed at a location "upstream" of the binding sites 112 to compensate for the displacement during filling. Additionally or alternatively, the positioning of the droplet may substantially be left as it is, but the distribution of the magnetic beads in the droplet is changed such that the beads concentrate in a sub-region located "upstream". This can be achieved in a modification of the arrangement of FIG. 1 by pulling the beads in the bead droplet by a magnetic field towards the inlet of the reaction chamber (which may e.g. be at the left side of the processing device in FIGS. 1, 2) during the drying process. During the filling of the cartridge, the beads are then transported towards the outlet again, however they now end up above the binding sites 112.

The aforementioned approach can also be used when magnetic beads are applied to the cover 114 (top of the chamber), where the bead re-dispersion is also important. A droplet of matrix material, volatile carrier, and magnetic beads may hence also be deposited on the cover 114 and dried while a magnetic field pulls the magnetic particles to an "upstream" position within the droplet.

In a concrete embodiment of the described procedures, magnetic beads MP have been dosed in a quantity of about 50 nl on the base-part 111 on top of an antibody spot 112. The magnetic beads were comprised in a solution containing buffering components, salts and sucrose, among other things. After dosing the magnetic beads were dried for about 30 min at about 37° C. During this drying process an external magnetic field was applied on a distance of about 5 mm with a magnet that creates a field that is parallel to the reaction surface. After the drying phase the magnetic field was removed and the cartridge was processed using the normal procedure.

The reduction of non-specific binding was measured for different preparation procedures using a single bead detection technology. This technology provides a surface specific image showing the amount of magnetic beads bound to the surface. The amount of magnetic beads can directly be translated to a FTIR signal change.

Figure 3:
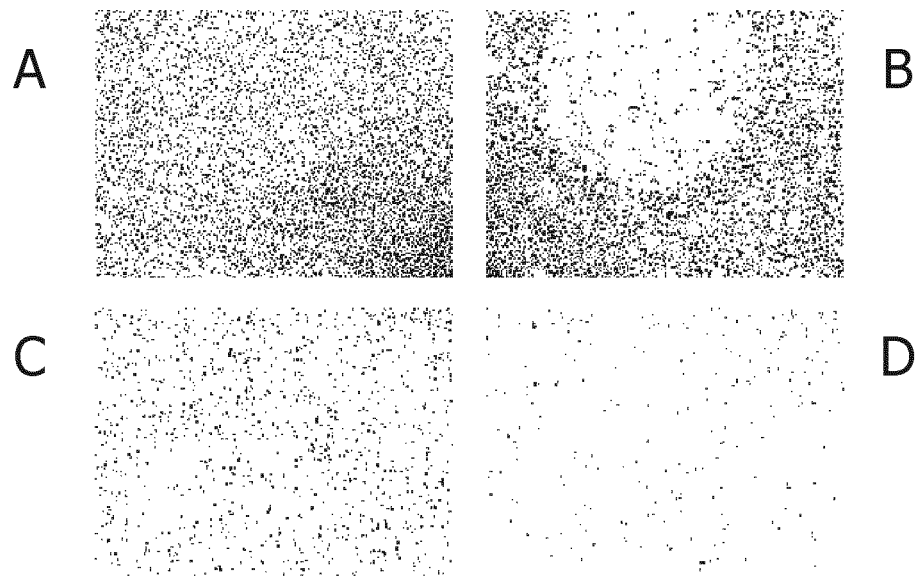
FIG. 3 shows photos of magnetic beads bound to reaction surfaces in tests using different manufacturing methods.

FIG. 3 shows four images of reaction surfaces obtained by single magnetic bead imaging during a washing phase of a blank sample (plasma pool containing no target analyte). Each dark spot in the images corresponds to a magnetic bead bound to the reaction surface. The preparation conditions for the four images were as follows:

Image A (top left) shows a reaction surface obtained without any blocking treatment and without application of a magnetic field during drying.

Image B (top right) shows a reaction surface obtained without any blocking treatment but with application of a magnetic field during drying.

Image C (bottom left) shows a reaction surface obtained with blocking treatment and without application of a magnetic field during drying.

Image D (bottom right) shows a reaction surface obtained with blocking treatment and with application of a magnetic field during drying.

The images of FIG. 3 clearly show that applying a magnetic field during the drying phase reduces the non-specific interaction time of the magnetic beads with the reaction surface. When applying a blocking step next to the magnetic field, the amount of non-specific interaction is further reduced and brought back to a level which is usually only seen when the magnetic beads are dosed on the laminate, so have no interaction with the surface during drying.

Figure 4:
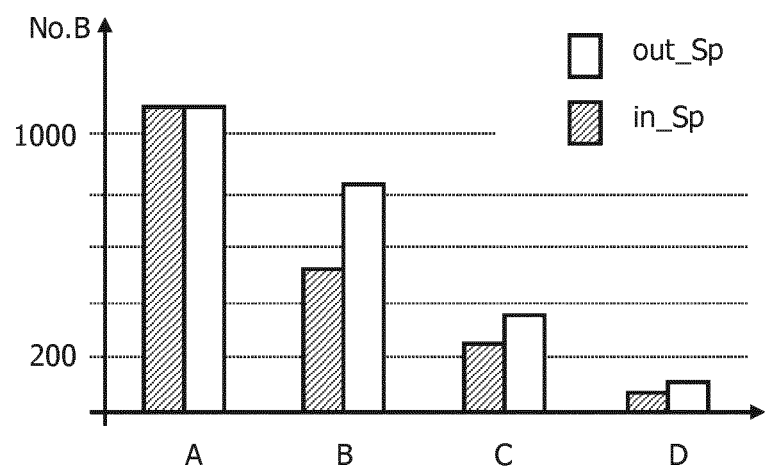
FIG. 4 is a diagram representing the counts (vertical axis) of bound magnetic particles in the tests of FIG. 3.

FIG. 4 shows in a diagram the results of a magnetic bead count for the four different configurations A, B, C, and D shown in FIG. 3 (the vertical axis indicating the counted number of beads). The hatched bars "in_Sp" correspond to a magnetic bead count (corrected for area) inside the region of interest (ROI) of the printed antibody spots. The white bars "out_Sp" correspond to the area outside the printed spots.

The magnetic bead count is for the configuration of test "D" on par with the bead count seen when the magnetic beads are dosed on the laminate and thus when there is no interaction of the magnetic beads with the surface during processing.

In comparison to a technology in which magnetic beads are provided on a lid of the cartridge, the described approach has an advantage when measurements in a "dirty matrix" (i.e. blood) are made. This is because placing the magnetic beads on top of the reaction/binding surface reduces variation and increases assay performance. This is due to the fact that the blood-cells make the transportation of the beads from the laminate to the reaction/binding surface difficult.

In summary, embodiments of the invention have been described in which a mixture of magnetic particles, a matrix material, and a volatile carrier is deposited onto binding sites of a reaction surface. The deposited mixture is then dried while the magnetic particles are pulled away from the reaction surface by a magnetic field. Thus unspecific binding of magnetic particles to the binding sites can be prevented.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method for manufacturing a processing device comprising magnetic particles, said method comprising the following steps:
   a) depositing a liquid mixture comprising magnetic particles, a matrix material, and a volatile carrier onto a surface of the device;
   b) pulling the magnetic particles of the mixture away from said surface to a desired location within the mixture; and
   c) drying the mixture by removing the volatile carrier.

2. The method according to claim 1, wherein the magnetic particles of the mixture are pulled by a magnetic field in step b).

3. The method according to claim 2, wherein a non-zero gradient of the magnetic field is oriented substantially perpendicular to said surface.

4. The method according to claim 1, wherein said surface is a reaction surface which is at least locally coated with binding sites that can specifically bind target substances.

5. The method according to claim 1, wherein said surface is treated with a blocking substance that binds to binding points before the depositing step a).

6. The method according to claim 1, wherein the volatile carrier comprises an aqueous liquid.

7. The method according to claim 1, wherein the magnetic matrix material comprises at least one material selected from the group consisting of sucrose, salt, buffer components, blocking components and assay reagents.

8. The method according to claim 1, wherein that the matrix material is water soluble.

9. The method according to claim 1, wherein that the magnetic particles are disposed upstream of a target location with respect to the intended flow of a fluid in the processing device.

10. The method according to claim 9, wherein that the target location comprises binding sites that can specifically bind target substances.

* * * * *